US010195071B2

(12) United States Patent
Vezina et al.

(10) Patent No.: US 10,195,071 B2
(45) Date of Patent: Feb. 5, 2019

(54) DEVICE AND METHOD FOR THE TREATMENT OF BRUXISM

(71) Applicants: William Karl Vezina, Stillwater, MN (US); Sue Margaret Vezina, Stillwater, MN (US)

(72) Inventors: William Karl Vezina, Stillwater, MN (US); Sue Margaret Vezina, Stillwater, MN (US)

(*) Notice: Subject to any disclaimer, the term of this patent is extended or adjusted under 35 U.S.C. 154(b) by 611 days.

(21) Appl. No.: 14/945,709

(22) Filed: Nov. 19, 2015

(65) Prior Publication Data

US 2016/0143770 A1 May 26, 2016

Related U.S. Application Data

(60) Provisional application No. 62/083,073, filed on Nov. 21, 2014.

(51) Int. Cl.
*A61F 5/56* (2006.01)
(52) U.S. Cl.
CPC ........ *A61F 5/566* (2013.01); *A61F 2005/563* (2013.01)
(58) Field of Classification Search
CPC ...... A61F 5/566; A61F 5/56; A61F 2005/563; A61F 5/58; A61C 7/08; A61C 19/063; A61B 5/4547; A61B 5/4552; A61B 5/4557; A61B 5/682; A61B 5/0534; A63B 71/085; A63B 2071/086; A63B 2017/088
See application file for complete search history.

(56) References Cited

U.S. PATENT DOCUMENTS

| | | | |
|---|---|---|---|
| 4,976,618 A * | 12/1990 | Anderson | A61C 19/04 433/215 |
| 5,078,153 A | 1/1992 | Nordlander et al. | |
| 5,823,787 A | 10/1998 | Gonzalez et al. | |
| 6,164,278 A | 12/2000 | Nissani | |
| 7,263,998 B2 | 9/2007 | Miller | |
| 8,020,276 B2 * | 9/2011 | Thornton | A61F 5/56 128/206.21 |
| 8,763,613 B2 | 7/2014 | Chodorow | |
| 8,961,437 B2 | 2/2015 | Al-Tawil | |
| 9,827,137 B2 * | 11/2017 | Schlatter | A61F 5/56 |
| 2017/0196727 A1 * | 7/2017 | Giridharagopalan | A61F 5/566 |

OTHER PUBLICATIONS

Dr. Lee Weinstein, "SleepGuard Biofeedback Headband", retrieved from www.mysleepguard.com.
(Continued)

*Primary Examiner* — Tarla R Patel
(74) *Attorney, Agent, or Firm* — Kagan Binder, PLLC (57) ABSTRACT

Bruxism, which is a human medical condition characterized by clenching of the jaw and/or grinding of teeth, leads to conditions such as severe tooth wear and Temporomandibular Joint (TMJ) Disorder. Described herein is a biofeedback device that utilizes the human physiological reflex to open the mouth when the nasal airway is obstructed. The device and method blocks the nasal airway while clenching, but allows nasal respiration while not clenching. Clenching of the jaw and breathing through the mouth cannot happen simultaneously while unconscious.

17 Claims, 5 Drawing Sheets

(56) References Cited

OTHER PUBLICATIONS

Wikipedia, "Bruxism", retrieved from https://en.wikipedia.org/wiki/Bruxism.

National Institute of Dental and Craniofacial Research, "Prevalence of TMJD and Its Signs and Symptoms", retrieved from http://www.nidcr.nih.gov/DataStatistics/FindDataByTopic/FacialPain/PrevalenceTMJD.htm.

Dao et al., "Oral Splints: the Crutches for Temporomandibular Disorders and Bruxism?", Crit. Rev. Oral Biol. Med. 9(3), pp. 345-361 (1998).

\* cited by examiner figure 1 figure 2 figure 3 figure 4 figure 5

DEVICE AND METHOD FOR THE TREATMENT OF BRUXISM

PRIORITY CLAIM

The present nonprovisional patent application claims the benefit of and priority to, under 35 USC § 119(e), U.S. Provisional Patent Application No. 62/083,073, filed Nov. 21, 2014, entitled "DEVICE AND METHOD FOR THE TREATMENT OF BRUXISM BY UTILIZING THE PHYSIOLOGICAL REFLEX WHICH CAUSES THE HUMAN BODY TO OPEN THE MOUTH WHEN THE NASAL AIRWAY IS BLOCKED", the entirety of which is incorporated herein by reference.

BACKGROUND OF THE INVENTION

Bruxism is a detrimental human medical condition characterized by clenching of the jaw and/or grinding of teeth. Bruxism leads to conditions such as severe tooth wear and Temporomandibular Joint (TMJ) Disorder. TMJ is characterized by painful inflammation of the jaw joint and sinuses as well as headaches and neck pain. It is estimated that 33% of the population has bruxism to some extent and 5-12% of the population suffers from severe TMJ symptoms. Bruxism manifests itself nocturnally, while the user is unconscious and unable to control the clenching and grinding behavior. This is known as sleep bruxism.

There currently are no completely effective treatments for sleep bruxism. The treatments that have demonstrated some effectiveness, such as biofeedback devices, rely on waking the user to cease the clenching behavior. This is accomplished with negative feedback (loud noise or foul tasting fluid) during the clenching behavior. These feedback methods are limited in their effectiveness because bruxism typically occurs during, or when coming out of, a very deep sleep when the user is slow to wake. These methods are also unpopular because they can provide feedback before the user is fully asleep (given an inadvertent bite-down). Also, they have been known to disturb the user's bed partner without waking the user.

SUMMARY OF THE INVENTION

While researching improved treatments for sleep bruxism, it was observed that sufferers of sleep bruxism have reported relief from clenching when they are suffering from the common cold. The blockage of the nasal airway, as caused by the common cold, causes the user to breathe through his/her mouth only. The relief from sleep bruxism is because humans cannot clench their teeth/jaw and breathe through his/her mouth simultaneously while unconscious.

The invention is based on the physiological reflex that causes the human body to open the mouth when the nasal airway is blocked. The device blocks the nasal airway while clenching, but also allows nasal respiration while not clenching. The invention consists of a clench sensor and a nasal airway obstructor. When the clench pressure is detected, the nasal airway is blocked until the user stops clenching. The clenching, unclenching, and resumed nasal respiration sequence has been demonstrated to occur without waking the user. It has been verified that blockage of the nasal airway (airway inclusion) while unconscious is not normally dangerous. People, on average, have 5-10 airway inclusions per hour naturally while asleep.

In various example embodiments, the invention, which obstructs the user's nasal airway upon detecting the clenching behavior, has two primary components including a clench or pressure sensor and a nasal airway obstructor. The clench sensor can be embedded in a custom fit mouthpiece, or rely on external orofacial indications caused by the clenching behavior. The sensor can communicate the clenching behavior to the nasal airway obstructor electrically, electromagnetically, mechanically, via fluid power transmission, or other similar mechanisms. The nasal airway obstructor can be an airway valve mounted within the air passage of a nasal manifold (pillow), hood, or mask type device, or it can be a device that physically plugs the user's nose by collapsing the nostrils or plugging the nostrils with any manner of stopper devices.

The device may include a one-piece system or a two-piece system. With the one-piece system, the mouthpiece and associated clench sensor and nasal airway obstructor apparatus are connected via a high strength strut. The entire apparatus is anchored via upper teeth to the hard palate. The two-piece system detects the clench behavior with the clench sensor, and obstructs the nasal airway with a separate nasal airway obstructor. The two separate devices can communicate electrically, electromagnetically, mechanically, or via fluid power transmission. The two components of the two-piece system may be connected via a flexible conduit.

In use, the device functions by first sensing a bite or clenching action with a clench sensor, which triggers a nasal airway obstructing device. Upon blockage of the nasal airway, the human body instinctively reacts by opening the mouth (unclenching the jaw) to allow oral respiration. Upon unclenching of the jaw, the device re-opens the nasal airway to allow nasal respiration.

In an example embodiment, a device for treating bruxism includes a mouthpiece and a nasal airway obstruction member. The mouthpiece includes a sensor for sensing a mechanical or clenching pressure, and is configured to emit a signal upon reaching a pressure threshold. The nasal airway obstruction member is operatively connected to the mouthpiece and is capable of obstructing nasal respiration upon receiving the signal from the sensor.

In an alternative embodiment, the device may include a nasal manifold, a hood, a mask, a physical plug, or a combination thereof. A nasal hood assembly may include a cup shaped hood and a strap coupled to the hood to maintain an airtight seal around a user's nasal airway.

In yet another embodiment, the mouthpiece and nasal airway obstruction member are connected via a strut. Alternatively, the connection between the mouthpiece and the nasal airway obstruction member is established electrically, electromagnetically, mechanically, or via fluid or hydraulic transmission. Still further, the clench sensor and nasal airway obstruction member may communicate utilizing mechanical or electrical feedback from an external musculoskeletal structure of a user's orofacial region. In yet another embodiment, the pressure sensor of the device may be an electrical switch, a strain gauge, a piezoelectric crystal, a fluidic device, or a combination thereof.

In still yet another embodiment, the nasal airway obstruction member is actuated when the pressure sensor detects clenching by the user, which causes the user to open his/her mouth to allow oral respiration. The nasal airway obstruction member may include a horizontal bar member with a nasal plunger located at each distal end of the bar member, and each nasal plunger is located adjacent to a nasal airway of the user. The nasal plunger may project towards and obstruct the nasal airway upon receiving a signal from the pressure sensor. In an embodiment, the mouthpiece may be anchored to the user's upper teeth to the hard palate. The nasal airway obstructor fits over a user's nose. In another embodiment, the device may be powered by physical clenching of a user, an electrical battery pack, an external power supply, or a combination thereof.

A method of treating bruxism includes providing the device comprising a mouthpiece and nasal airway obstruction member. The mouthpiece and associated pressure sensor may be anchored to the upper teeth, lower teeth, or both of a user and the nasal airway obstruction member is placed adjacent to the user's nasal region. Upon receiving a signal from the pressure sensor the nasal airway passage of the user is obstructed. After a predetermined amount of time the nasal airway passage blockage is released. In an alternative method, when the user unclenches, the nasal airway obstruction member ceases obstruction of nasal respiration. Still further, a data processing unit is capable of recording when the user clenches and unclenches his/her jaw. The data processing unit configured to communicate with a smart device and a software applet.

DETAILED DESCRIPTION OF THE INVENTION

Described herein is a device for the treatment of bruxism. A first embodiment may include a one-piece system, and a second embodiment may include a two-piece system. In either embodiment, the device includes a clench sensor and a nasal airway obstructor.

Figure 1:
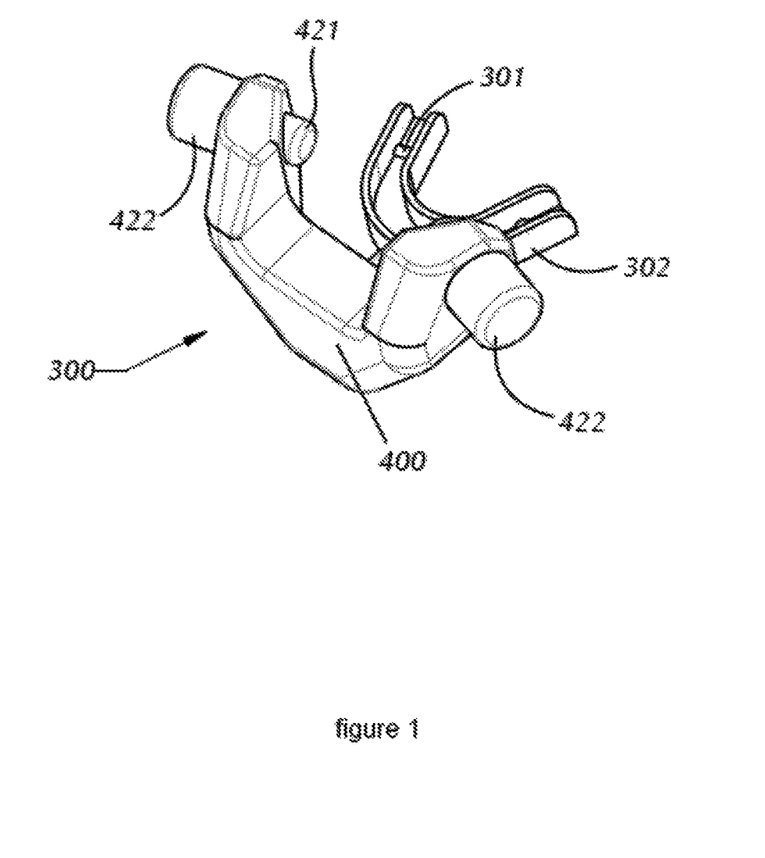
FIG. 1 illustrates an example embodiment of a bruxism treatment device.

FIG. 1 illustrates an example embodiment of a bruxism treatment device 300. Bruxism treatment device 300 includes mouthpiece 302, clench sensor 301, and nasal airway obstructor 400. In an example embodiment, clench sensor 301 is embedded within mouthpiece 302. Alternatively, clench sensor 301 may be disposed on a top or bottom of the mouthpiece 302. Nasal airway obstructor 400 includes nasal obstructors 421 and electro-mechanism drives 422. The mouthpiece 302 is operatively connected to nasal airway obstructor 400 to provide a means of communication.

Figure 2:
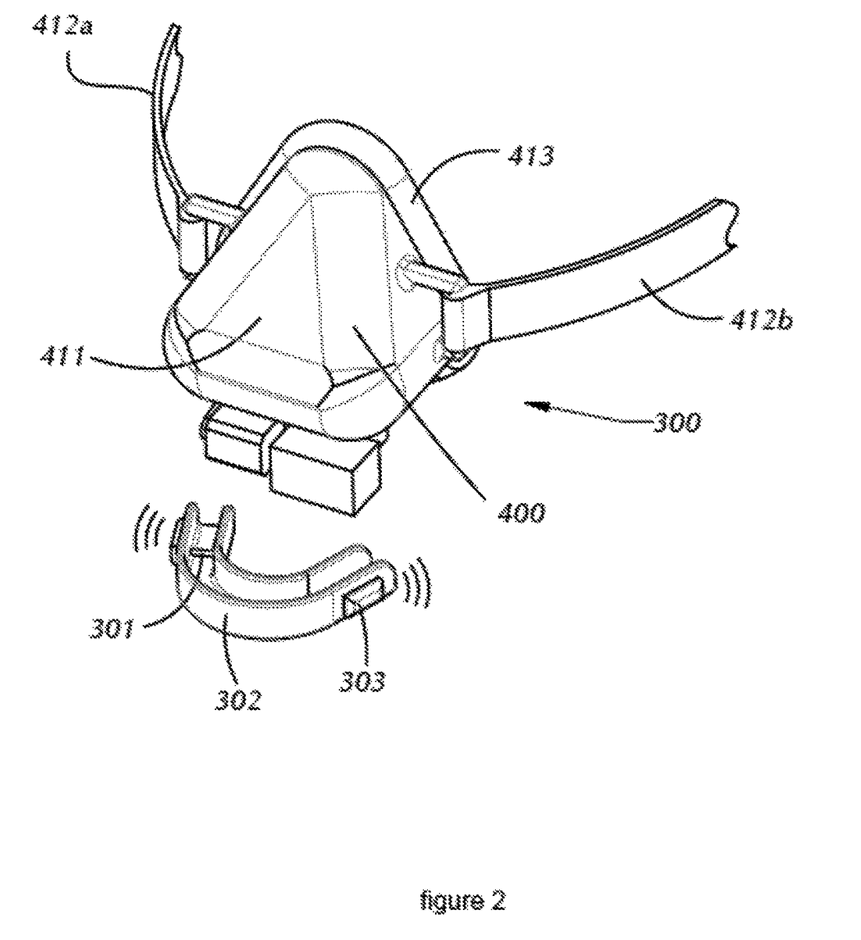
FIG. 2 shows an alternative example embodiment of a bruxism treatment device.

FIG. 2 illustrates an example embodiment of a two-piece bruxism treatment device 300. Mouthpiece 302 may be separate from nasal airway obstructor 400. Mouthpiece 302 includes clench sensor 301 and wireless signal transmitter 303. Nasal airway obstructor 400 includes hood 411, seal 413, and straps 412a, 412b. Hood 411 may be sized and shaped to cover a user's nose, for example in a cup or hood configuration. Seal 413 encircles an edge of hood 411 to create seal of hood 411 against a user's face. Straps 412a, 412b extend from either side of nasal airway obstruct 400 and around a user's head.

Figure 3:
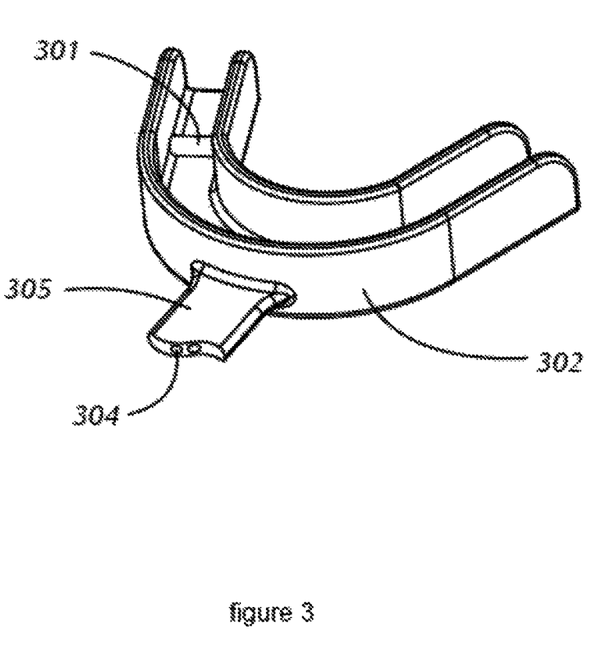
FIG. 3 shows an example embodiment of a mouthpiece.

The mouthpiece 302 is shown in more detail at FIG. 3. Mouthpiece 302 include at least one clench sensor 301. Clench sensor 301 detects the clenching behavior of a user and sends a feedback signal (biofeedback) to the nasal airway obstructor 400. In one embodiment of the invention, the clench sensor 301 is embedded in mouthpiece 302. The clench sensor 301 can be an electrical switch, strain gauge, piezoelectric crystal, fluidic displacement device, or other similar mechanism. A wireless signal transmitter 303 (not shown) can be embedded in the mouthpiece 302 to transmit the clench data to the data processing unit 416 electromagnetically in either a one-piece system or a two-piece system. Alternatively, in a one-piece system, a clench sensor 301 can communicate the clench behavior to the nasal airway obstructor 400 via passages 304, which are contained within a conduit connection 305. Conduit connection 305 extends through the lips of the user to the data processing unit 416 of the nasal airway obstructor 400.

Mouthpiece 302 may be a variety of sizes and shapes. In an embodiment, the mouthpiece 302 may be custom fitted to the user's teeth. An example mouthpiece 302 may cover the top teeth, the bottom teeth, or both. Example materials of a mouthpiece 302 may include an elastic material such as rubber or plastic, or may be an inelastic material such as other plastics with little or no flexibility.

The clench signal can be transmitted electrically, electromagnetically, mechanically, via fluid power transmission, or other similar mechanism. In an alternative embodiment, bruxism treatment device 300 may accomplish clench detection utilizing physical or electrical feedback from the external musculoskeletal structure of the user's orofacial region.

Figure 4:
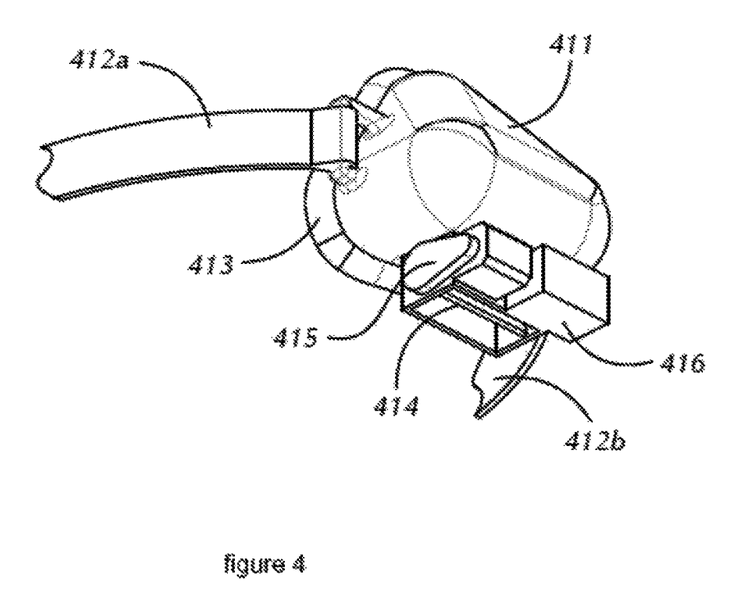
FIG. 4 shows an example embodiment of a nasal obstructor.

The nasal airway obstructor 400 obstructs the user's nasal airway to prevent the user from breathing through their nose. In an embodiment of the invention shown in FIG. 4, the nasal airway obstructor 400 is comprised of a nasal hood assembly, which is comprised of a cup-shaped hood 411 and is held to the user's face with straps 412a, 412b and maintains an airtight seal 413 to the user's face and encloses the nose. An airway valve 414 may control airflow into hood 411. The airway valve 414 can be a high flow, low resistance valve. An example airway valve 414 may be a motorized butterfly valve with a data processing unit. The airway valve 414 is actuated by an electro-mechanical drive 415 and is controlled by a data processing unit 416 to allow normal, unobstructed respiration through the hood 411 when the user is not clenching. When the user is clenching, the data processing unit 416 controls the airway valve 414 via the electro-mechanical drive 415 to obstruct the user's air supply partially or fully.

The bruxism treatment device 300 can be powered by the physical clenching action of the user, an electrical battery pack contained within the assembly, or an external power supply. The mouthpiece 302 of FIG. 3 and the nasal airway obstructor 400 of FIG. 4 can be used together to form a two-piece system. When clench sensor 301 receives a signal that the user is clenching his/her jaw, a signal is sent to nasal airway obstructor 400, which blocks air flow to the nostrils, thereby forcing the user to breathe through his/her mouth. The bruxism treatment device 300 may also include a power source. The power source may be external to the device to provide power to the device through a battery or electrical cord. Alternatively, the bruxism treatment device 300 may be powered by the physical clenching action of a user.

Figure 5:
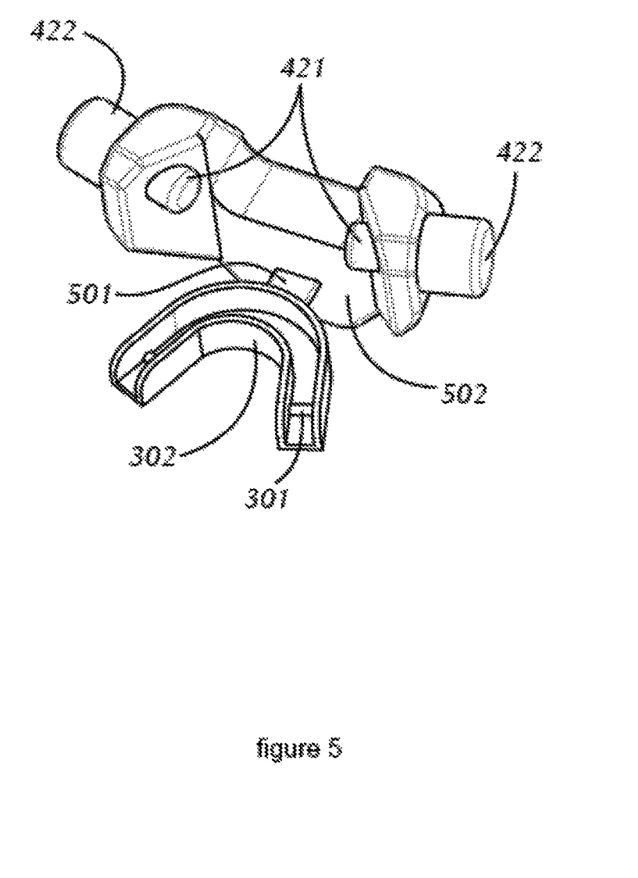
FIG. 5 illustrates an example embodiment of the bruxism treatment device of FIG. 1.

FIG. 5 illustrates an example embodiment of a one-piece bruxism treatment device 300. The clench sensor 301 is incorporated into the mouthpiece 302 and is connected to the nasal airway obstructor 400 via a rigid strut 501. The rigid strut 501 is routed through the user's lips to the nasal airway obstructor 400. The bruxism treatment device 300 is anchored via the mouth piece 302 and upper teeth to the user's hard palate. The rigid foundation of the hard palate allows the nasal obstructors 421 to be held via the rigid housing 502 in the correct orientation about the user's nostrils. Nasal obstructors 421 function by the actuation of two linear actuators that are held in the correct orientation as to collapse the user's nostrils and seal-off the airway when actuated. The linear actuators can be driven by electromechanical drives 422, mechanical power transmission, or fluidic power transmission (hydraulic or pneumatic). The rigid housing 502 of the bruxism treatment device 300 may contain a data processing unit 416, power source (not shown), or other power transmission apparatus from the clench sensor 301. Other power transmission apparatuses may be mechanical or fluid.

The one-piece configuration could also utilize a hood 411, a nasal pillow type manifold (not shown), or any other manner of controllable nasal airway stoppers as a nasal airway obstructor 400. Other nasal airway stoppers may include a mask, a physical plug, or other similar mechanism. Nasal airway obstructor 400 may be rigid, or alternatively may be pliable. These nasal airway obstructions may communication with the mouthpiece via an electrical, electromagnetic, mechanical, fluid transmission, hydraulic transmission, or other similar mechanism.

The described invention may utilize data processing algorithms to control the airway obstructor in a way to best treat the user. This may include limiting the degree to which the airway is obstructed and the amount of time that the airway is obstructed. Data collection is also possible for the purpose of tracking the user's clenching behavior and improvement. Such data may be transmittable to a computer, phone, a smart device, or other electronic device for review.

In use, the mouthpiece 302 is anchored to a user's upper teeth or lower teeth and the nasal airway obstructor 400 is placed over a user's nasal region. When a user clenches his/her jaw, a signal is sent to the nasal airway obstructor, which blocks air flow to the nostrils of the user, forcing the user to breathe through his/her mouth. Airflow to the nostrils is restored after a predetermined period of time. Such a time period may be 5 seconds, 10 seconds, or up to 30 seconds. Alternatively, a time period may be once the user unclenches his/her jaw.

The following patents are incorporated by reference in their entireties: U.S. Pat. Nos. 5,078,153; 6,164,278; and 8,020,276.

While the invention has been described above in terms of specific embodiments, it is to be understood that the invention is not limited to these disclosed embodiments. Upon reading the teachings of this disclosure many modifications and other embodiments of the invention will come to mind of those skilled in the art to which this invention pertains, and which are intended to be and are covered by both this disclosure and the appended claims. It is indeed intended that the scope of the invention should be determined by proper interpretation and construction of the appended claims and their legal equivalents, as understood by those of skill in the art relying upon the disclosure in this specification and the attached drawings.

What is claimed is:

1. A device for the treatment of bruxism comprising:
    a mouthpiece including a pressure sensor for sensing a mechanical or clenching pressure, the sensor configured to emit a signal upon reaching a pressure threshold;
    a nasal airway obstruction member operatively connected to the mouthpiece, the nasal airway obstruction member capable of obstructing nasal respiration upon receiving the signal from the pressure sensor; and wherein the nasal airway obstruction member includes a horizontal bar member with nasal plunger located at each distal end of the bar member, each nasal plunger located adjacent to a nasal airway of a user and projecting toward and obstructing the nasal airway upon receiving the signal from the pressure sensor.

2. The device of claim 1, wherein the nasal airway obstruction member includes at least one of a nasal manifold, a hood, a mask, a physical plug, and actuators to collapse nostrils.

3. The device of claim 1 wherein the mouthpiece and the nasal airway obstruction member are connected via a strut.

4. The device of claim 1 wherein the operative connection between the mouthpiece and the nasal airway obstruction member is established electrically, electromagnetically, mechanically, or via fluid or hydraulic transmission.

5. The device of claim 1 wherein the sensor and the nasal airway obstruction member communicate utilizing at least one of mechanical or electrical feedback from an external musculoskeletal structure of a user's orofacial region.

6. The device of claim 1 wherein the pressure sensor is selected from the group consisting of an electrical switch, strain gauge, piezoelectric crystal, and fluidic displacement device.

7. The device of claim 1 wherein the nasal airway obstruction member includes a nasal hood assembly having a cup shaped hood and a strap coupled thereto to maintain an airtight seal around a user's nasal airway.

8. The device of claim 7 wherein the mouthpiece is anchored to upper teeth and to the hard palate.

9. The device of claim 1 wherein the nasal airway obstruction member is actuated when the pressure sensor detects a user clenching, thereby causing a user to open a mouth to allow oral respiration.

10. The device of claim 1 wherein the mouthpiece is anchored to upper teeth and to the hard palate.

11. The device of claim 1 wherein the device is powered by physical clenching action of the user, an electrical battery pack, or an external power supply.

12. A method of treating bruxism comprising:
    sensing a mechanical or clenching pressure via a mouthpiece, a pressure sensor configured to emit a signal upon reaching a pressure threshold, and a nasal airway obstruction member operatively connected to the mouthpiece, the nasal airway obstruction member capable of obstructing nasal respiration upon receiving a signal from the sensor; wherein the nasal airway obstruction member includes a horizontal bar member with nasal plunger located at each distal end of the bar member, each nasal plunger located adjacent to a nasal airway of a user and projecting toward and obstructing the nasal airway upon receiving the signal from the pressure sensor,
    anchoring the mouthpiece with the pressure sensor to at least one of an upper tooth and lower tooth of a user;
    securing the nasal airway obstruction member adjacent to or over a user's nasal region;
    obstructing the nasal airway of the user upon receiving the signal from the pressure sensor; and
    releasing the nasal obstruction after an elapse of a predefined time period.

13. The method of claim 12 wherein when the user unclenches, the nasal airway obstruction member ceases obstruction of nasal respiration.

14. The method of claim 12 wherein the sensor and the nasal airway obstruction member communicate utilizing physical or electrical feedback from the external musculoskeletal structure of the user's orofacial region.

15. The method of claim 12 wherein the mouthpiece and the nasal airway obstruction member are connected via a strut.

16. The method of claim 12 wherein the device comprises a data processing unit that is capable of recording when the user clenches the jaw.

17. The method of claim 16 wherein the data processing unit communicates with a wireless smart device and a software applet.

* * * * *